(12) United States Patent
Paul

(10) Patent No.: US 10,357,335 B2
(45) Date of Patent: Jul. 23, 2019

(54) ORTHODONTIC APPLIANCES FOR CORRECTING TEETH IRREGULARITIES AND FOR RETAINING THE POSITION OF TEETH

(71) Applicant: Jeff Paul, Fuquay-Varina, NC (US)

(72) Inventor: Jeff Paul, Fuquay-Varina, NC (US)

(73) Assignee: Apex Ortho Innovations, LLC, Fuquay Varina, NC (US)

( * ) Notice: Subject to any disclaimer, the term of this patent is extended or adjusted under 35 U.S.C. 154(b) by 157 days.

(21) Appl. No.: 14/487,314

(22) Filed: Sep. 16, 2014

(65) Prior Publication Data

US 2015/0086935 A1    Mar. 26, 2015

Related U.S. Application Data

(60) Provisional application No. 61/878,068, filed on Sep. 16, 2013.

(51) Int. Cl.
*A61C 7/00* (2006.01)
*A61C 7/08* (2006.01)

(52) U.S. Cl.
CPC ............... *A61C 7/00* (2013.01); *A61C 7/08* (2013.01); *A61C 2201/007* (2013.01)

(58) Field of Classification Search
CPC .. A61C 7/00; A61C 7/002; A61C 7/08; A61C 7/10; A61F 5/566
USPC ............................................................ 433/6
See application file for complete search history.

(56) References Cited

U.S. PATENT DOCUMENTS

| 1,139,170 | A | * | 5/1915 | Drissler et al. | A61C 7/00 433/21 |
|---|---|---|---|---|---|
| 1,142,467 | A | * | 6/1915 | Walker | A61C 7/00 433/21 |
| 4,026,023 | A | * | 5/1977 | Fisher | A61C 7/10 433/7 |
| 4,197,632 | A | | 4/1980 | Burstone et al. | |
| 4,573,914 | A | * | 3/1986 | Nord | A61C 7/10 433/18 |
| 4,637,796 | A | * | 1/1987 | Korn | A61C 7/00 433/7 |

(Continued)

FOREIGN PATENT DOCUMENTS

| EP | 1204383 B1 | 2/2007 |
|---|---|---|
| WO | 2010046879 A1 | 4/2010 |

OTHER PUBLICATIONS

International Preliminary Report on Patentability and Written Opinion of the International Searching Authority for PCT International Application No. PCT/US014/05575, dated Dec. 26, 2014.

(Continued)

*Primary Examiner* — Wade Miles
*Assistant Examiner* — Matthew P Saunders
(74) *Attorney, Agent, or Firm* — Forrest Firm, P.C.

(57) ABSTRACT

Orthodontic appliances for correcting teeth irregularities and for retaining the position of teeth are disclosed. According to an aspect, an orthodontic appliance may include an arch component configured to engage one of teeth and gums of a patient. Further, the orthodontic appliance may include a spring having a teeth engaging portion and an anchor portion. The teeth engaging portion may be shaped to engage the incisors of the patient. The anchor portion may be attached to the arch component.

18 Claims, 7 Drawing Sheets

(56) References Cited

U.S. PATENT DOCUMENTS

| | | | | | |
|---|---|---|---|---|---|
| 4,976,614 | A | * | 12/1990 | Tepper | A61C 7/00 433/18 |
| 5,096,416 | A | * | 3/1992 | Hulsink | A61C 7/08 433/6 |
| 5,376,001 | A | * | 12/1994 | Tepper | A61C 7/00 433/6 |
| 5,607,300 | A | * | 3/1997 | Tepper | A61C 7/00 433/24 |
| 6,332,774 | B1 | * | 12/2001 | Chikami | A61C 7/00 433/20 |
| 6,435,871 | B1 | * | 8/2002 | Inman et al. | A61C 7/00 433/7 |
| 7,887,324 | B2 | * | 2/2011 | Singh | A61C 7/10 433/24 |
| 8,062,031 | B2 | * | 11/2011 | Inman | A61C 7/10 433/18 |
| 8,192,196 | B2 | * | 6/2012 | Singh | A61C 7/10 433/7 |
| 2004/0185411 | A1 | * | 9/2004 | Graham | A61C 7/00 433/21 |
| 2007/0087300 | A1 | * | 4/2007 | Willison | A61C 7/12 433/6 |
| 2007/0184398 | A1 | * | 8/2007 | Cronauer | A61C 7/08 433/6 |
| 2011/0027743 | A1 | | 2/2011 | Cinader et al. | |
| 2011/0129786 | A1 | | 6/2011 | Chun et al. | |
| 2011/0236847 | A1 | * | 9/2011 | Hang | A61C 7/10 433/6 |
| 2011/0287377 | A1 | * | 11/2011 | Hang | A61C 7/10 433/7 |
| 2012/0129117 | A1 | | 5/2012 | McCance | |

OTHER PUBLICATIONS

International Search Report for PCT International Application No. PCT/US014/05575, dated Dec. 26, 2014.
Extended European Search Report dated Mar. 30, 2017 from related European Application No. 14844473.0.
Communication pursuant to Article 94(3) EPC issued in counterpart European Application No. 14844473.0 dated Jul. 3, 2018 (four (4) pages).

* cited by examiner

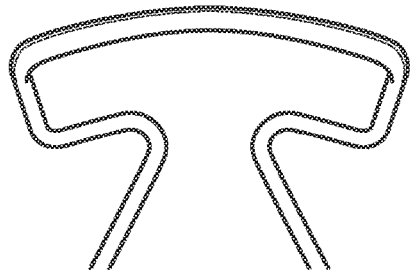 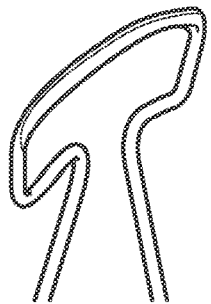 
FIG. 7A　　　FIG. 7B　　　FIG. 7C
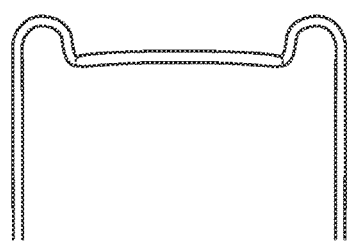 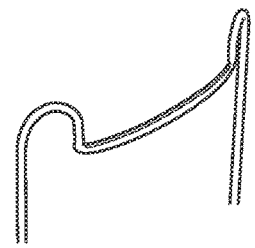 
FIG. 8A　　　FIG. 8B　　　FIG. 8C

__US 10,357,335 B2__

ORTHODONTIC APPLIANCES FOR CORRECTING TEETH IRREGULARITIES AND FOR RETAINING THE POSITION OF TEETH

CROSS REFERENCE TO RELATED APPLICATION

This application claims the benefit of and priority to U.S. Provisional Patent Application No. 61/878,068, filed Sep. 16, 2013 and titled ORTHODONTIC APPLIANCES FOR CORRECTING TEETH IRREGULARITIES AND FOR RETAINING THE POSITION OF TEETH; the disclosure of which is incorporated by reference herein in its entirety.

TECHNICAL FIELD

The present subject matter relates to orthodontic appliances, and more particularly to orthodontic appliances for correcting teeth irregularities and for retaining the position of teeth.

BACKGROUND

Various types of orthodontic appliances have been provided for correcting incisor irregularities and for retaining teeth in corrected position for either the lower or upper anterior teeth. Conventional spring retainers are made with acrylic covering the labial bow on the facial surfaces of the teeth and acrylic covering the spring on the lingual surfaces of the teeth. The points where the acrylic touches the teeth are critical wear areas. As the patient removes and inserts the retainer, the surfaces of the teeth can begin to wear the acrylic such that the retainer does not functional as well on subsequent uses. It is noted that the conventional retainer with acrylic covering the labial bow and the lingual spring are also manufactured on a model on which teeth have been reset to the doctor's ideal specifications. Because a small portion of the acrylic is wears each time the patient removes and reinserts the retainer, it is steadily changing from an appliance that is designed to the doctor's ideal arch to an appliance that is slightly off and getting worse every time because the acrylic, which is supposed to determine the final position of the teeth, is wearing down. In addition, because a conventional retainer is made of steel wire, it will require additional adjustment by the doctor in order to maintain vital constant pressure on the teeth.

Because conventional appliances wear and doctors do not have the ability to constantly hand adjust the appliance to an ideal configuration of the original model, improved orthodontic appliances are desired.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are orthodontic appliances for correcting teeth irregularities and for retaining the position of teeth. According to an aspect, an orthodontic appliance may include an arch component configured to engage one of teeth and gums of a patient. Further, the orthodontic appliance may include a spring having a teeth engaging portion and an anchor portion. The teeth engaging portion may be shaped to engage the incisors of the patient. The anchor portion may be attached to the arch component.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIGS. 7A-7C depict a top view, a ¾ perspective view, and a side view, respectively, of a spring for an appliance in accordance with embodiments of the present subject matter; and FIGS. 8A-8C depict a top view, a ¾ perspective view, and a side view, respectively, of a labial bow for an appliance in accordance with embodiments of the present subject matter.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
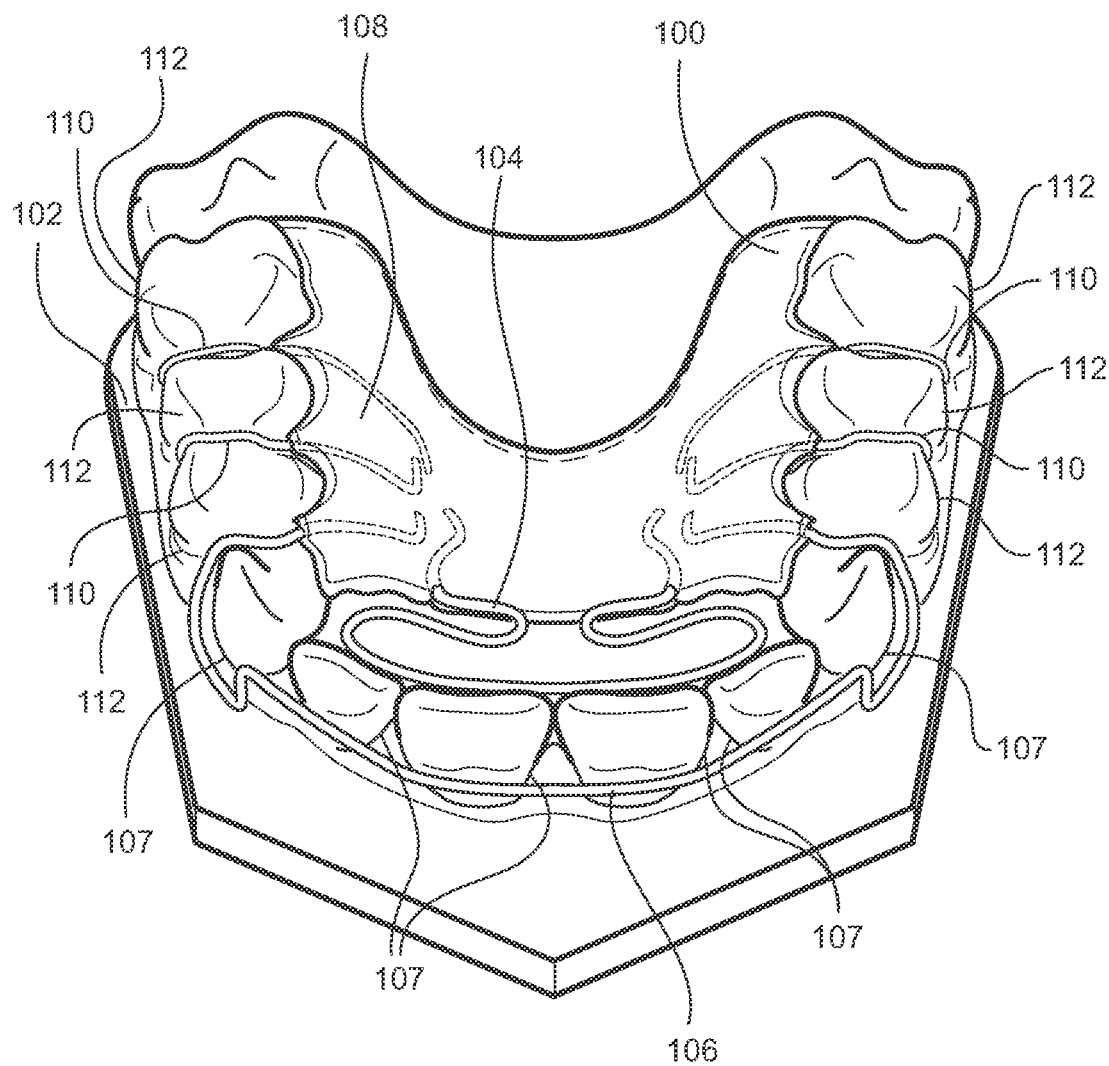
FIG. 1 is a front perspective view showing an example orthodontic appliance for correcting teeth irregularities and for retaining the position of teeth in accordance with embodiments of the present subject matter.

FIG. 1 illustrates a front perspective view showing an example orthodontic appliance 100 for correcting teeth irregularities and for retaining the position of teeth in accordance with embodiments of the present subject matter. In this example, the appliance 100 is a retainer and sized and shaped to fit to lower teeth. Referring to FIG. 1, the appliance 100 is placed in operational position with a model 102 of lower teeth. The appliance 100 includes a spring 104 made of beta titanium wire. Alternatively, the spring 104 can be made of any suitable metal or other material having shape memory properties such as, but not limited to, Ti—Mo—Ag and Ti—Mo—Sn.

Because the appliance 100 of this example is constructed of beta titanium wire, it is capable of a substantial range of movement without readjustment on the doctor's part. The appliance 100 may be manufactured on a model on which teeth have been reset to the doctor's expectations. The shape memory property of the beta titanium wire can allow it to remember that ideal arch form when it is positioned in the patient's mouth and can continue to apply constant pressure on the teeth until it has returned to the position at which it was originally manufactured.

In accordance with embodiment, the beta titanium wire can have one or more flat or substantially flat portions. For example, a flattened surface of the beta titanium wire may have a surface area that touches a tooth (e.g., incisor) by as much as 60% greater than a round-shaped wire.

The appliance 100 includes a bow 106 having a loop and configured to engage one of teeth 107 and gums of a patient corresponding to the model 102. During manufacture, the bow 106 may be formed to established informal contact with the anterior incisors. As shown in FIG. 1, the loop of the bow 106 may begin in the mesial ⅓ of the cuspids. The loop of the bow 106 may end in the interproximal between the cuspid and first bicuspid.

The appliance 100 may include an arch component 108. The arch component 108 may be configured to hold multiple wires 110 that extend outward for engaging teeth 112. The arch component 108 may hold the bow 106 in place. The arch component 108 may be made of a rigid plastic or any other suitable material.

Figure 2:
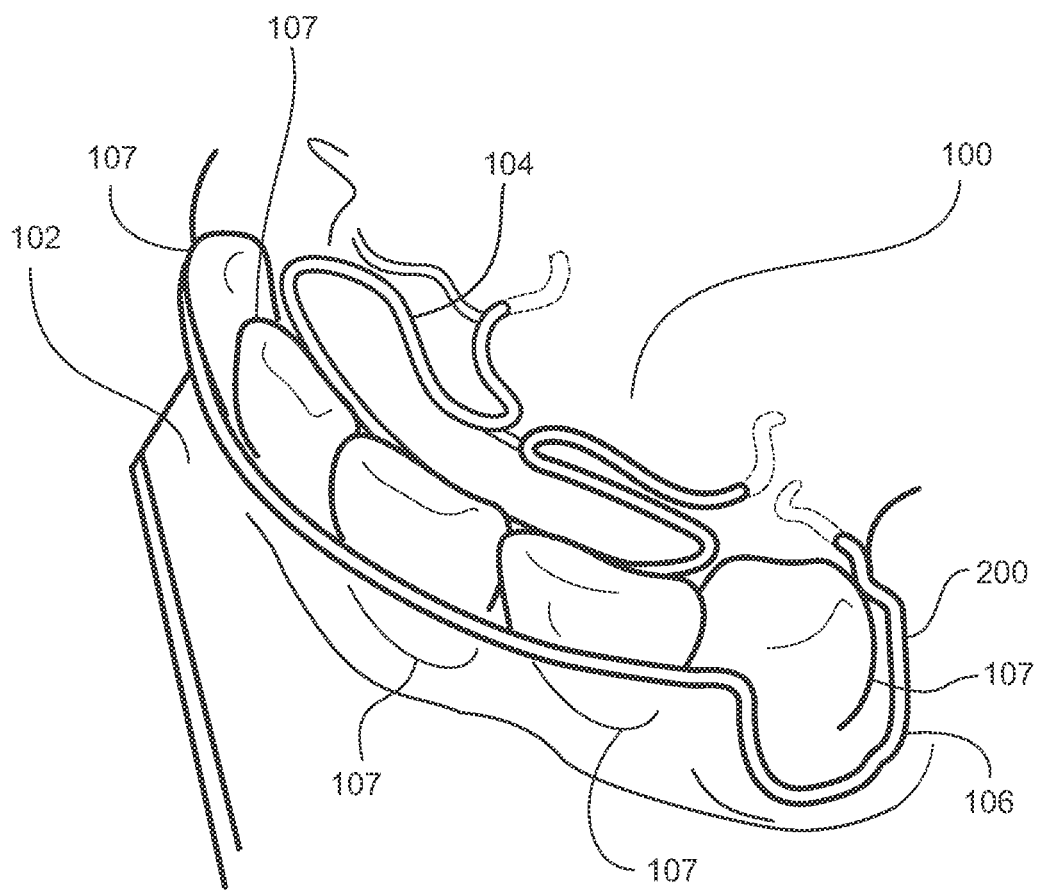
FIG. 2 is a perspective view of a front portion of the appliance shown in FIG. 1 along with text describing positioning of components of the appliance with respect to teeth and gums of the model in accordance with embodiments of the present subject matter.

FIG. 2 illustrates a perspective view of a front portion of the appliance 100 shown in FIG. 1. Referring to FIG. 2, a loop 200 of the arch bow 106 begins at the mesial ⅓ of the cuspid and ends between the cuspid and first bicuspid. The arch bow 106 establishes contact with all anterior incisors as shown.

Figure 3:
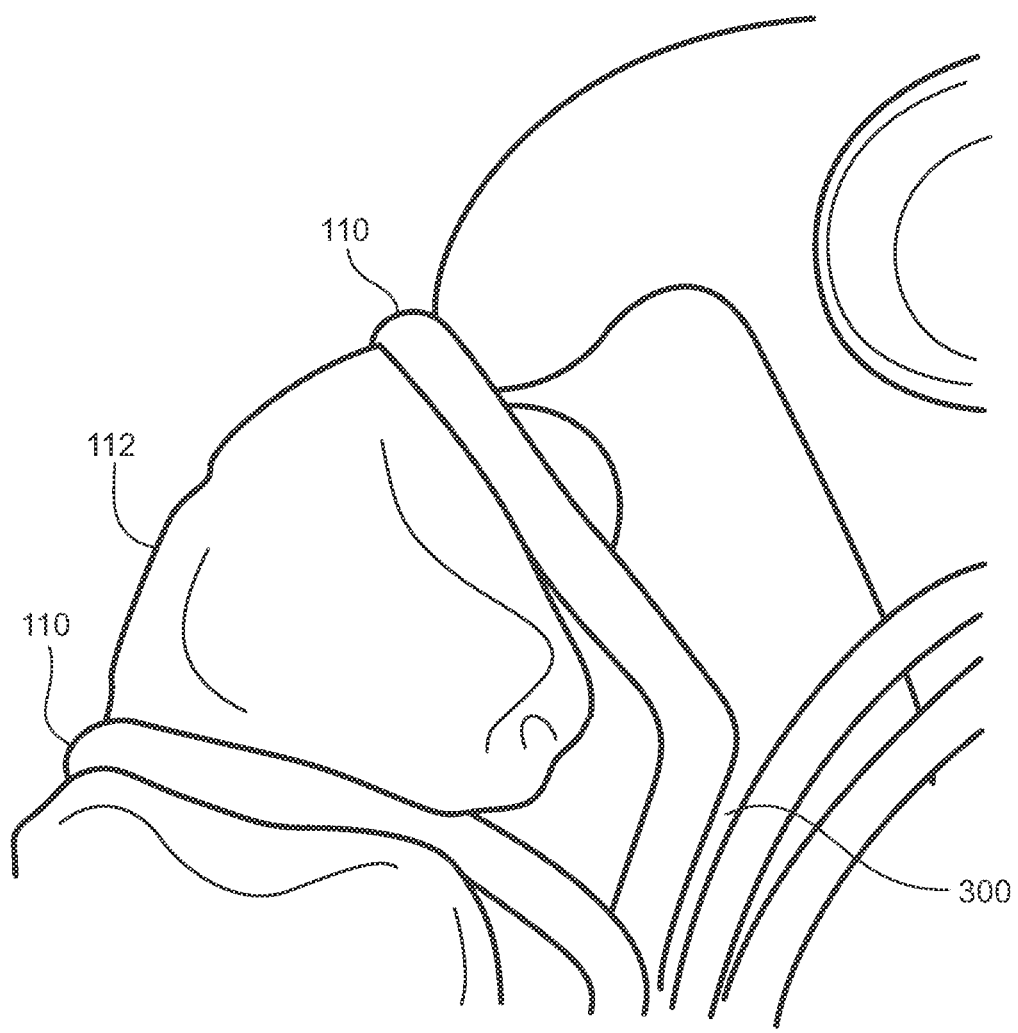
FIG. 3 is a perspective view of the appliance shown in FIG. 1 fitting to the teeth and gums in this manner in accordance with embodiments of the present subject matter.

FIG. 3 illustrates a perspective view of a side portion of the appliance 100 shown in FIG. 1. Referring to FIG. 3, the wires 110 provide intimate contact across occlusion and down to the gingiva. In this example, a 0.5 mm space 300 is provided between the wire 110 and tissue from the gingiva to the end of the retention foot.

Figure 4:
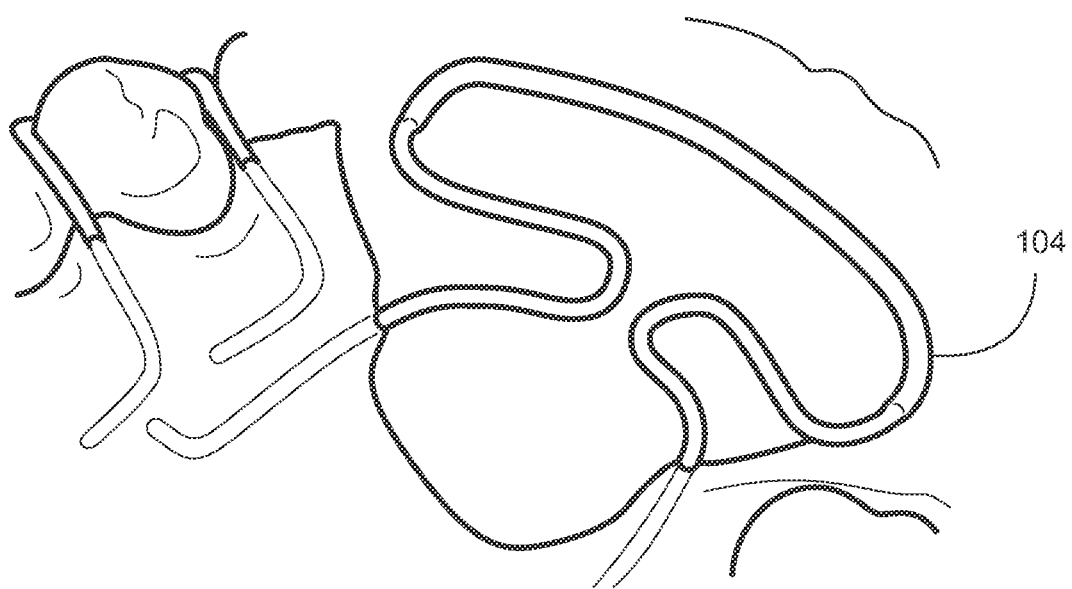
FIG. 4 is a perspective view of the appliance shown in FIG. 1 fitting to the teeth and gums in this manner in accordance with embodiments of the present subject matter.

In another step of manufacture, the tag end of the wire may be formed to establish intimate contact across the occlusion between the cuspid and the first bicuspid following down to the gingiva. The wire may lose contact with the tissue once the gingiva is reached. From the gingiva to the end of the foot, 0.5 mm or any suitable distance of clear space may be left between the wire and the tissue so that acrylic can fully encase the wire. FIG. 4 illustrates a perspective view of the appliance fitting to the teeth and gums in this manner in accordance with embodiments of the present subject matter.

In another step of manufacture, the proper width of the spring 104 may be from the distal of the lateral to the distal of the opposite lateral. Intimate contact may be made with the lingual surfaces of the incisors. The wire may be adjusted to lay flat against the lingual surface of the teeth above the cingulum of all of the incisors. The tag ends of the wire may be adjusted such that they go at least half way up into the palatal vault with about 0.5 mm of space or any other suitable spacing between the wire and tissue so that the wire is completely or substantially encased in acrylic or any other suitable material. FIG. 4 illustrates a perspective view of the appliance fitting to the teeth and gums in this manner in accordance with embodiments of the present subject matter.

In another step of manufacture, clasping components for the appliance 100 can be made and shaped. The amount of clasping needed may be dependent upon the amount of movement the appliance 100 may be expected to deliver. For example, if all four anteriors need to be reset or stripped, then the appliance may be finished with Adam's clasps and ball clasps. If only two teeth need to be reset or stripped, then Adam's clasps may be adequate for retention. If no teeth need to be reset or stripped, then ball clasps may provide sufficient clasping.

Figure 5A:
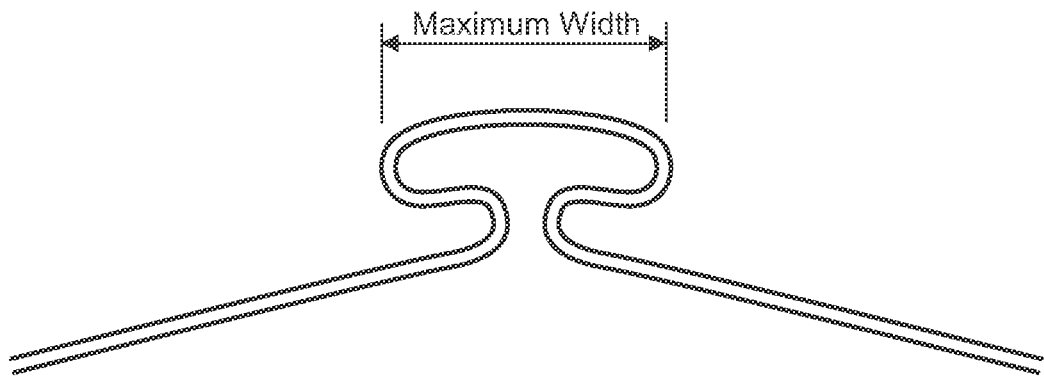
FIGS. 5A and 5B are top views of different formed wires for use in manufacture of a spring on an appliance in accordance with embodiments of the present subject matter.
Figure 5B:
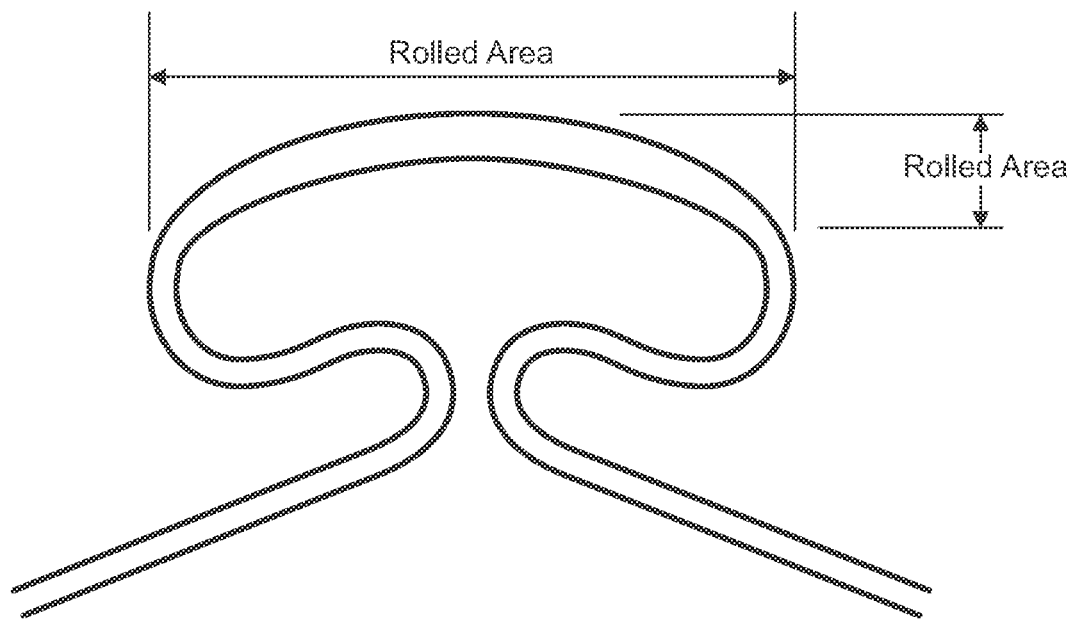

In accordance with embodiments of the present subject matter, a kit for manufacture of an appliance as disclosed herein may include one or more formed wires to function as a spring as disclosed herein. FIGS. 5A and 5B illustrate top views of different formed wires for use in manufacture of a spring on an appliance in accordance with embodiments of the present subject matter. The spring sizes can have any of the following maximum widths 20.0 mm, 22.0 mm, 27.0 mm, 30.0 mm, 34.0 mm, or any other suitable width. As an example, springs may be formed from 0.036 beta titanium wire with an initial segment length of between 140 mm and 178 mm depending on the final spring width. The final spring width is a description of the width of the rolled area of the spring at its widest point (See e.g., FIG. 5A). The spring can be formed from round wire in the various sizes (maximum width) and subsequently rolled to a thickness of approximately 0.5 mm from the top of the spring to the point of its maximum width. The remainder of the spring wire is round. FIG. 5A depicts an example of the formed wire prior to rolling, and FIG. 5B depicts an example of the formed wire after rolling.

Figure 6A:
FIGS. 6A-6C depict various steps for forming a bow of an appliance in accordance with embodiments of the present subject matter.
Figure 6B:
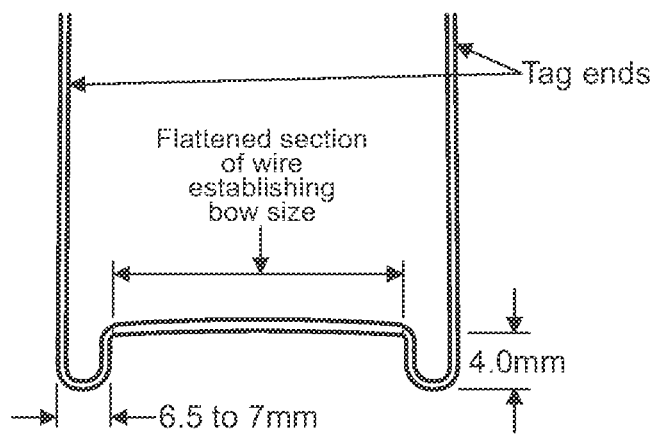
Figure 6C:
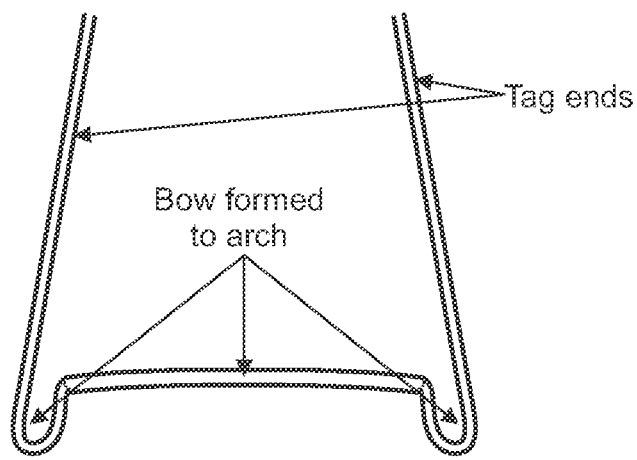

Labial bows can be formed from 0.036 beta titanium wire with an initial segment length of 178 mm. FIGS. 6A-6C illustrate various steps for forming a bow in accordance with embodiments of the present subject matter. The spring sizes can have any of the following flattened section widths 25.0 mm, 26.0 mm, 31.5 mm, 34.5 mm, 37.5 mm, 40.5 mm, 43.5 mm, 46.5 mm, 49.5 mm or any other suitable width. In an example, the center section may be flattened out to about 0.5 mm thickness with a rolling mill. The flattening process may begin in the center of the wire and may extend out in both directions until the required distance is flattened (See e.g., FIG. 6A). For example to make a bow of flattened section width 25.0 mm, the wire can be flattened to 0.5 mm for a distance of 12.5 mm on either side of center.

Once flattened, the loops may be formed (See e.g., FIG. 6B). The loops can be between 6.5 mm and 7.0 mm across and about 4.0 mm deep. When the loops are formed, the wire can be formed into an arch with the tag ends left for a lab technician to work across the occlusion and into the acrylic (See e.g., FIG. 6C).

FIGS. 7A-7C illustrate a top view, a ¾ perspective view, and a side view, respectively, of a spring for an appliance in accordance with embodiments of the present subject matter. The spring can have, for example, any of the following sizes: spring size 1-18.0 mm (maximum width); spring size 2-20.0 mm (maximum width); spring size 3-22.0 mm (maximum width); spring size 4-24.0 mm (maximum width); spring size 5-27.0 mm (maximum width); and spring size 6-30.0 mm (maximum width). The spring can be formed from round wire in the various sizes (maximum width) and subsequently rolled to a suitable thickness from the top of the spring to the point of its maximum width. The remainder of the spring wire may be round.

FIGS. 8A-8C illustrate a top view, a ¾ perspective view, and a side view, respectively, of a labial bow for an appliance in accordance with embodiments of the present subject matter. The bow can have, for example, any of the following sizes: size 1-25.0 mm (flattened width section); size 2-28.0 mm (flattened width section); size 3-31.5 mm (flattened width section); size 4-34.5 mm (flattened width section); size 5-37.5 mm (flattened width section); size 6-40.5 mm (flattened width section); size 7-43.5 mm (flattened width section); size 8-46.5 mm (flattened width section); and size 9-49.5 mm (flattened width section). The spring can be formed from round wire in the various sizes (maximum width) and subsequently rolled to a suitable thickness from the top of the spring to the point of its maximum width. The remainder of the spring wire may be round.

An example advantage of an appliance as disclosed herein is that greater rotational force may be applied to teeth. This means that the force needed to rotate and push the teeth into an ideal position determined by the doctor may be greater, and therefore more effective with the beta titanium spring retainer than with a conventional spring retainer. This is due to two factors. First, because there is no acrylic on the spring or the bow to wear out, the direction of force applied by the spring and bow throughout the entire course of treatment remains the same as at the time it was manufactured on that model that had the teeth set to the doctor's ideal specifications. Second, because the spring is made of beta titanium wire with a memory, it can "remember" that ideal position that the teeth were set to on the model and because of the property of the wire, as opposed to steel, may not require constant readjustment by the doctor.

Another example advantage of an appliance as disclosed herein is that greater shape memory is provided as compared to stainless steel used in conventional appliances. The conventional spring is made of stainless wire and may run out of resilient force to push the teeth to that original ideal position set on the model. This can require hand adjustment by the doctor and the chances of him duplicating that original force can be slim. In addition, the acrylic, because of wear, is now different than at the time of manufacture so it becomes even less likely that he will be applying the proper force, in the proper direction after his or her adjustments.

The beta titanium spring as disclosed herein can "remember" the position and direction of force to which it was originally manufactured and because there is no acrylic wear and alter the direction and strength of force, it can continue to apply constant pressure, in the proper direction throughout a course of treatment.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. An orthodontic appliance comprising:
   a structural component;
   a labial bow consisting of a single, continuous wire at least partially comprised of memory metal being embedded in contact with the structural component and shaped to engage a labial and/or buccal surface of anterior teeth from a distal of a left cuspid to a distal of a right cuspid;
   an engaging component consisting of a single, continuous wire at least partially comprised of memory metal defining two anchor portions, two curved portions, a surface, and a lingual portion, wherein each of the two anchor portions are embedded in contact with the structural component,
   wherein the lingual portion is positioned between the structural component and the labial bow for forming a space to hold the anterior teeth in the shape defined by the labial bow,
   wherein the two curved portions extend between one of the two anchor portions and the lingual portion for applying constant pressure and a rotational force to the anterior teeth via the lingual portion,
   wherein a width of the engaging component extends from a distal of a right lateral to a distal of a left lateral.

2. The orthodontic appliance of claim 1, wherein the engaging component is shaped to engage the lingual surface of the incisors.

3. The orthodontic appliance of claim 1, wherein the lingual portion is shaped and positioned to lay substantially flat upon the lingual surface of the anterior teeth above the cingulum.

4. The orthodontic appliance of claim 1, wherein the surface is for engaging the incisors, wherein a width of the surface is between about 20 mm and about 34 mm.

5. The orthodontic appliance of claim 1, wherein the memory metal comprises beta titanium.

6. The orthodontic appliance of claim 5, wherein the beta titanium comprises one of Ti—Mo—Ag and Ti—Mo—Sn.

7. The orthodontic appliance of claim 1, wherein each of the two curved portions includes an S-shape.

8. The orthodontic appliance of claim 1, wherein each of the two curved portions consist essentially of an S-shape.

9. The orthodontic appliance of claim 1, wherein the curved portion includes a flattened portion.

10. A method for treating patient teeth, the method comprising:
    providing an orthodontic appliance, wherein the orthodontic appliance comprises:
    a structural component;
    a labial bow consisting of a single, continuous wire at least partially comprised of memory metal being embedded in contact with the structural component and shaped to engage a labial and/or buccal surface of anterior teeth from a distal of a left cuspid to a distal of a right cuspid;
    an engaging component consisting of a single, continuous wire at least partially comprised of memory metal defining two anchor portions, two curved portions, a surface, and a lingual portion,
    wherein each of the two anchor portions are embedded in contact with the structural component,
    wherein the lingual portion is positioned between the structural component and the labial bow for forming a space to hold the anterior teeth in the shape defined by the labial bow,
    wherein the two curved portions extend between one of the two anchor portions and the lingual portion for applying constant pressure and a rotational force to the anterior teeth via the lingual portion,
    wherein a width of the engaging component extends from a distal of a right lateral to a distal of a left lateral.

11. The method of claim 10, wherein the engaging component is shaped to engage the lingual surface of the incisors.

12. The method of claim 10, wherein the lingual portion is shaped and positioned to lay substantially flat upon the lingual surface of the anterior teeth above the cingulum.

13. The method of claim 10, wherein the surface is for engaging the incisors, wherein a width of the surface is between about 20 mm and about 34 mm.

14. The method of claim 10, wherein the memory metal comprises beta titanium.

15. The method of claim 14, wherein the beta titanium comprises one of Ti—Mo—Ag and Ti—Mo—Sn.

16. The method of claim 10, wherein each of the two curved portions includes an S-shape.

17. The method of claim 10, wherein each of the two curved portions consist essentially of an S-shape.

18. The method of claim 10, wherein the curved portion includes a flattened portion.

* * * * *